(12) United States Patent
Warner et al.

(10) Patent No.: US 11,990,239 B2
(45) Date of Patent: May 21, 2024

(54) SYSTEM AND METHOD FOR ANALYZING NOISE IN ELECTROPHYSIOLOGY STUDIES

(71) Applicant: GE Precision Healthcare LLC, Wauwatosa, WI (US)

(72) Inventors: Adrian Francis Warner, Delafield, WI (US); Daniel Richard Schneidewend, Menomonee Falls, WI (US); Mark Kohls, Delafield, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 519 days.

(21) Appl. No.: 16/509,782

(22) Filed: Jul. 12, 2019

(65) Prior Publication Data

US 2021/0012895 A1    Jan. 14, 2021

(51) Int. Cl.
*G16H 50/20* (2018.01)
*G06N 3/08* (2023.01)

(52) U.S. Cl.
CPC .............. *G16H 50/20* (2018.01); *G06N 3/08* (2013.01)

(58) Field of Classification Search
CPC ................................. G16H 50/20; G16N 3/08
See application file for complete search history.

(56) References Cited

U.S. PATENT DOCUMENTS

| | | | |
|---|---|---|---|
| 3,858,575 A | 1/1975 | Rose | |
| 5,010,887 A | 4/1991 | Thornander | |
| 9,342,732 B2 | 5/2016 | Harper | |
| 9,679,042 B2 | 6/2017 | Vlack et al. | |
| 2008/0147441 A1* | 6/2008 | Kil | G06Q 40/08 705/2 |
| 2008/0167567 A1* | 7/2008 | Bashour | A61B 5/352 600/521 |
| 2010/0317983 A1 | 12/2010 | Vajdic | |
| 2011/0082712 A1* | 4/2011 | Eberhardt, III | G16Z 99/00 705/4 |
| 2011/0224988 A1 | 9/2011 | Mahajan et al. | |
| 2012/0323132 A1* | 12/2012 | Warner | G16H 40/63 600/509 |
| 2015/0012222 A1* | 1/2015 | Warner | A61B 5/316 702/19 |
| 2015/0051452 A1* | 2/2015 | Ciaccio | G06F 17/14 600/407 |

(Continued)

OTHER PUBLICATIONS

University of Maryland Medical Center. "Can Your Doctor Correctly Read A Critical Heart Test? Improving Accuracy Of Electrocardiogram Interpretation." ScienceDaily. ScienceDaily, Nov. 3, 2008. <www.sciencedaily.com/releases/2008/10/081031102051.htm>.*

(Continued)

*Primary Examiner* — Jay M. Patel
(74) *Attorney, Agent, or Firm* — Grogan, Tuccillo & Vanderleeden, LLP

(57) ABSTRACT

A system for analyzing noise in one or more electrophysiology studies is provided. The system includes at least one processor and at least one memory device. The memory device stores an application that adapts the at least one processor to: identify, based at least in part on a machine learning model, one or more noise fingerprints within data derived at least in part from one or more study signals acquired from one or more patients during the one or more electrophysiology studies.

14 Claims, 7 Drawing Sheets

(56) References Cited

U.S. PATENT DOCUMENTS

2016/0364544 A1* 12/2016 Das .................... A61B 5/02055
2017/0112401 A1* 4/2017 Rapin .................... A61B 5/316
2017/0277656 A1* 9/2017 John .................... G06F 1/3287

OTHER PUBLICATIONS

Umera Banu, et al., "A Survey on Sources of Noise and Advanced Noise Removal Techniques of Biosignals", International Journal on Emerging Technologies, 2016, pp. 8-13, ISSN No. (Online): 2249-3255, Published by Research Trend, Website: www.researchtrend.net. https://www.researchtrend.net/ijet/pdf/3%20ICRIET-106.pdf.
Jaspreet Singh, "Noise in Bio-electrical Signals", Slides 1-36, Published in Technology, Jun. 22, 2017. https://www.slideshare.net/jassimehrok330/noise-in-bio-electric-signals.

* cited by examiner

SYSTEM AND METHOD FOR ANALYZING NOISE IN ELECTROPHYSIOLOGY STUDIES

CROSS-REFERENCE TO RELATED APPLICATIONS

This Application hereby incorporates U.S. patent application Ser. No. 13/934,723, filed Jul. 3, 2013 and now issued as U.S. Pat. No. 10,172,563, in its entirety.

TECHNICAL FIELD

Embodiments of the invention relate generally to electronic signal monitoring and, more specifically, to a system and method for analyzing noise in electrophysiology studies.

DISCUSSION OF ART

Electrocardiography ("ECG") studies record the electrical activity and pathways of a heart to identify, measure and diagnose arrhythmias. To accomplish this, ECGs utilize electrodes that are combined into pairs, the output of which are referred to as a lead. ECG leads are used in electrophysiology ("EP") studies, which assess electrical activity through the use of catheters placed in the heart through veins or arteries. More specifically, surface ECG leads attached to the patient are used as the reference for the intra cardiac signals from the catheters. That is, they apply a voltage reference to the patient for measurement by other leads.

In the electrophysiology context, ECG and intra cardiac leads may encounter line frequency noise, magnetic noise and/or noise from muscle tremors. Study noise may result from the use of wireless electrical devices, ablation equipment, the attachment of multiple medical devices to a subject, ungrounded electrical extension cords, electrical sockets, high-energy consumption equipment, and the like. In addition, the leads have to measure relatively small electrical signals from the patient, less than 20 uV in some instances. As will be appreciated, given the above considerations, achieving acceptable study recordings may be challenging and eliminating/reducing study noise is an important consideration.

In view of the above, it is desirable to accurately and efficiently identify sources of noise, and quantify the effects of noise, in electronic signal monitoring studies such as EP studies and the like, so that the sources may be removed.

BRIEF DESCRIPTION

In an embodiment, a system for analyzing noise in one or more electrophysiology studies is provided. The system includes at least one processor and at least one memory device. The memory device stores an application that adapts the at least one processor to: identify, based at least in part on a machine learning model, one or more noise fingerprints within data derived at least in part from one or more study signals acquired from one or more patients during the one or more electrophysiology studies.

In another embodiment, a method for analyzing noise in one or more electrophysiology studies is provided. The method includes identifying, based at least in part on a machine learning model executing on at least one processor, one or more noise fingerprints within data derived at least in part from one or more study signals acquired from one or more patients during the one or more electrophysiology studies.

In yet another embodiment, a non-transitory computer readable medium including instructions is provided. The instructions adapt at least one processor to: identify, based at least in part on a machine learning model, one or more noise fingerprints within data derived at least in part from one or more study signals acquired from one or more patients during one or more electrophysiology studies.

DRAWINGS

The present invention will be better understood from reading the following description of non-limiting embodiments, with reference to the attached drawings, wherein below:

DETAILED DESCRIPTION

Figure 1:
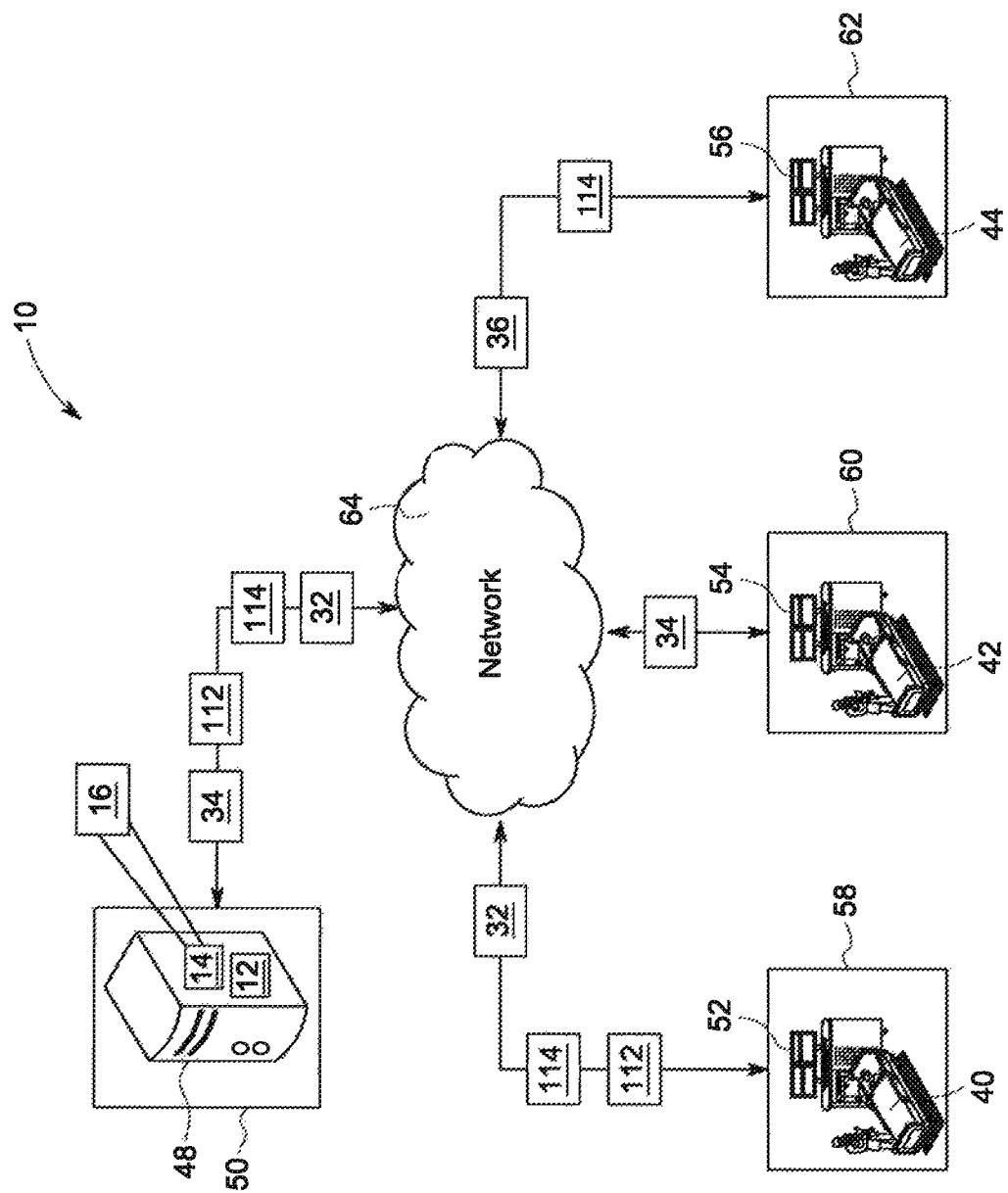
FIG. 1 is a diagram of a system for analyzing noise in one or more EP studies, in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. As used herein, the term "noise fingerprint" means one or more characteristics of a EP signal that correspond to a particular noise source.

Further, while the embodiments disclosed herein are described with respect to ECG studies, it is to be understood that embodiments of the present invention may be applicable to other types of systems that are subject to electrical noise, e.g., electroencephalogram ("EEG") studies.

Referring now to FIG. 1, the major components of a system 10 for analyzing noise in one or more EP studies, in accordance with an embodiment of the present invention, is shown. The system 10 includes at least one processor 12 and a memory device 14. The memory device 14 stores an application 16 that adapts/configures the at least one processor 12 to identify one or more noise fingerprints, e.g., 18, 20, 22, 24, 26, 28, 30 (FIGS. 2-8) within data 32, 34, 36 derived at least in part from one or more study signals 38 (FIGS. 2-8) acquired from one or more patients 40, 42, 44. As will be appreciated, and explained in greater detail below, identification of the noise fingerprints 18, 20, 22, 24, 26, 28, 30 is based at least in part on a machine learning model 46 (FIG. 10), e.g., an artificial neural network.

As shown in FIG. 1, the at least one processor 12 and memory device 14 may form part of a server 48 disposed at a first site/location 50, with the data 32, 34 and 36 being generated by EP devices 52, 54, 56 acquiring the study signals 38 from patients 40, 42 and 44 at multiple locations 58, 60, 62, and with the data 32, 34 and 36 electrically communicated to the server 48 over a network 64. While FIG. 1 depicts a single server 48 at a single location 50, it will be understood that, in embodiments, the application 16 may exist across multiple servers distributed over multiple locations, i.e., a Software as a Service (SAAS) cloud-based system. The network 64 may include private and public, e.g., the Internet, network components. In other embodiments, however, the network 64 may include only private physical network devices and communication lines.

The server site 50 and/or medical sites 58, 60 and/or 62 may be located at substantial distances from each other. As used herein, the term "server site" refers to the physical location(s) of the server(s) 48 executing the application 16. The term "medical site", as used herein, refers to a physical location at which an EP study used to generate the data 32, 34, 36 is performed. For example, the server site 50 may be one or more computing data centers located in a first U.S. State (or country outside of the U.S.), with sites 58, 60 and 62 being medical facilities located in different U.S. States (or countries outside of the U.S.). In some embodiments, however, the server site 50 may be located in the same building and/or medical campus as one or more of the medical sites 58, 60, 62.

Figure 2:
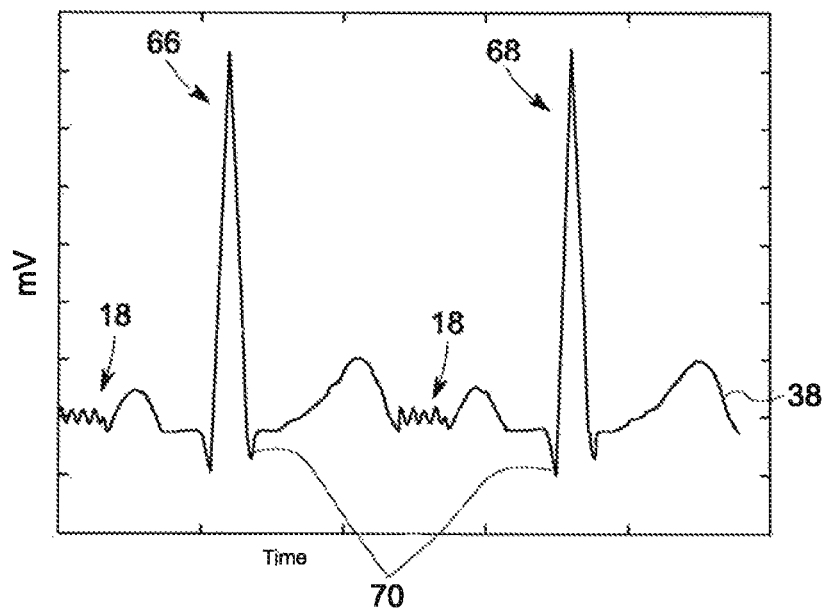
FIG. 2 is a diagram of a representative study signal of an EP study processed by the system of FIG. 1, in accordance with an embodiment of the present invention.
Figure 3:
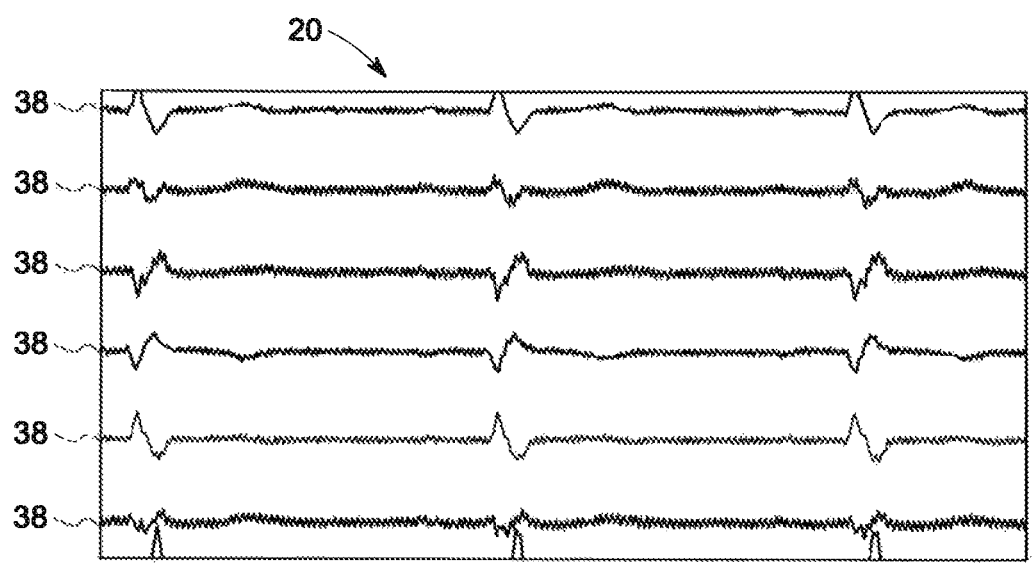
FIG. 3 is a diagram of an exemplary noise fingerprint identified by the system of FIG. 1, in accordance with an embodiment of the present invention.
Figure 4:
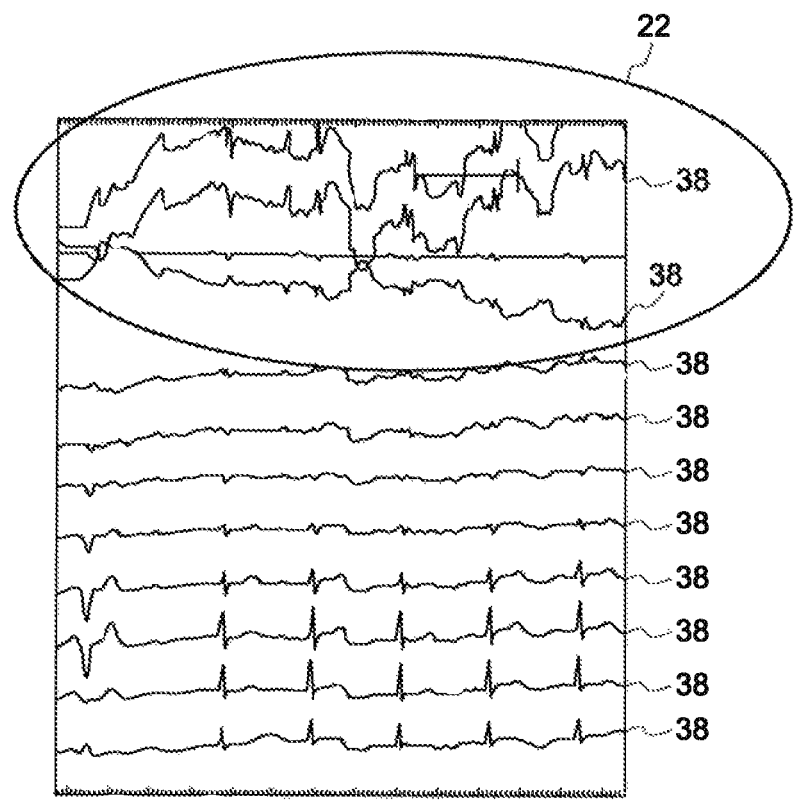
FIG. 4 is a diagram of another exemplary noise fingerprint identified by the system of FIG. 1, in accordance with an embodiment of the present invention.
Figure 5:
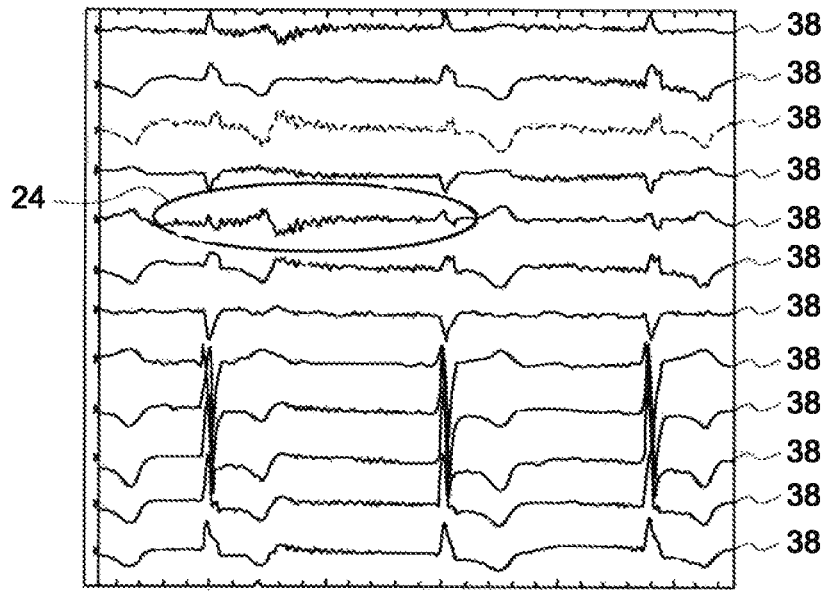
FIG. 5 is a diagram of still yet another exemplary noise fingerprint identified by the system of FIG. 1, in accordance with an embodiment of the present invention.
Figure 6:
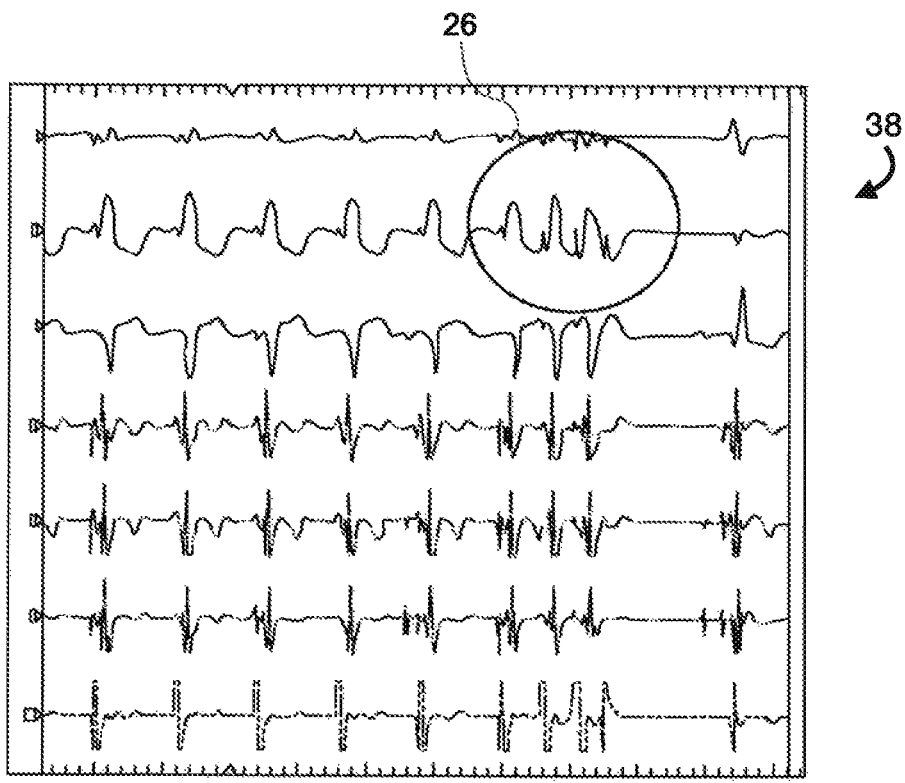
FIG. 6 is a diagram of still yet another exemplary noise fingerprint identified by the system of FIG. 1, in accordance with an embodiment of the present invention.
Figure 7:
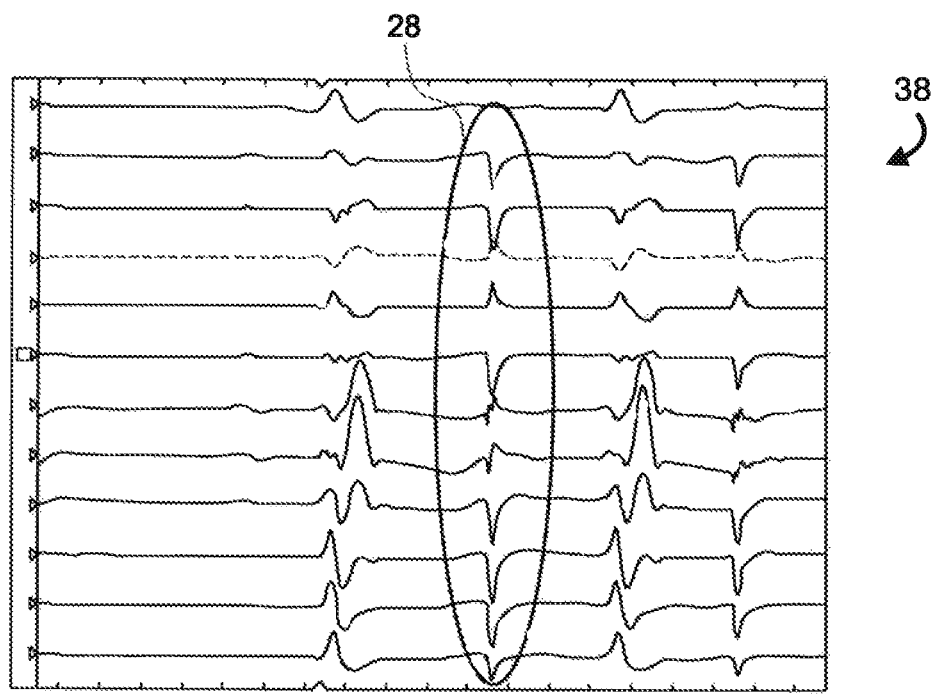
FIG. 7 is a diagram of still yet another exemplary noise fingerprint identified by the system of FIG. 1, in accordance with an embodiment of the present invention.
Figure 8:
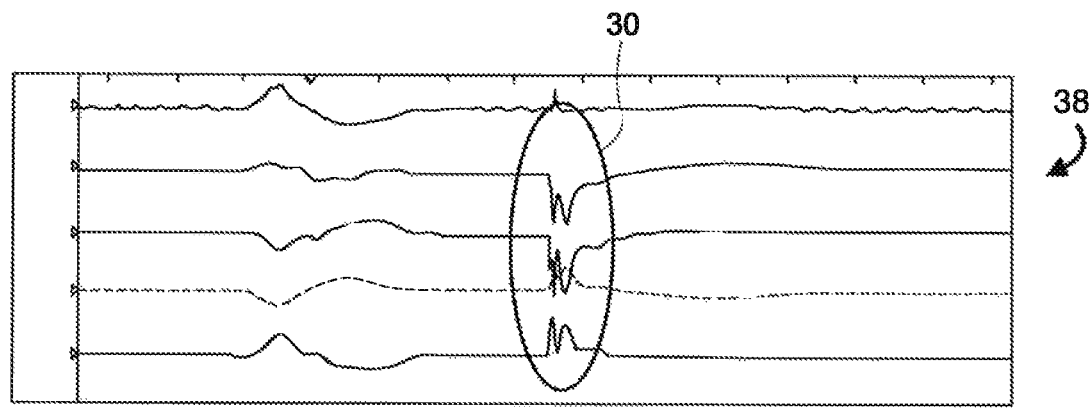
FIG. 8 is a diagram of still yet another exemplary noise fingerprint identified by the system of FIG. 1, in accordance with an embodiment of the present invention.
Figure 10:
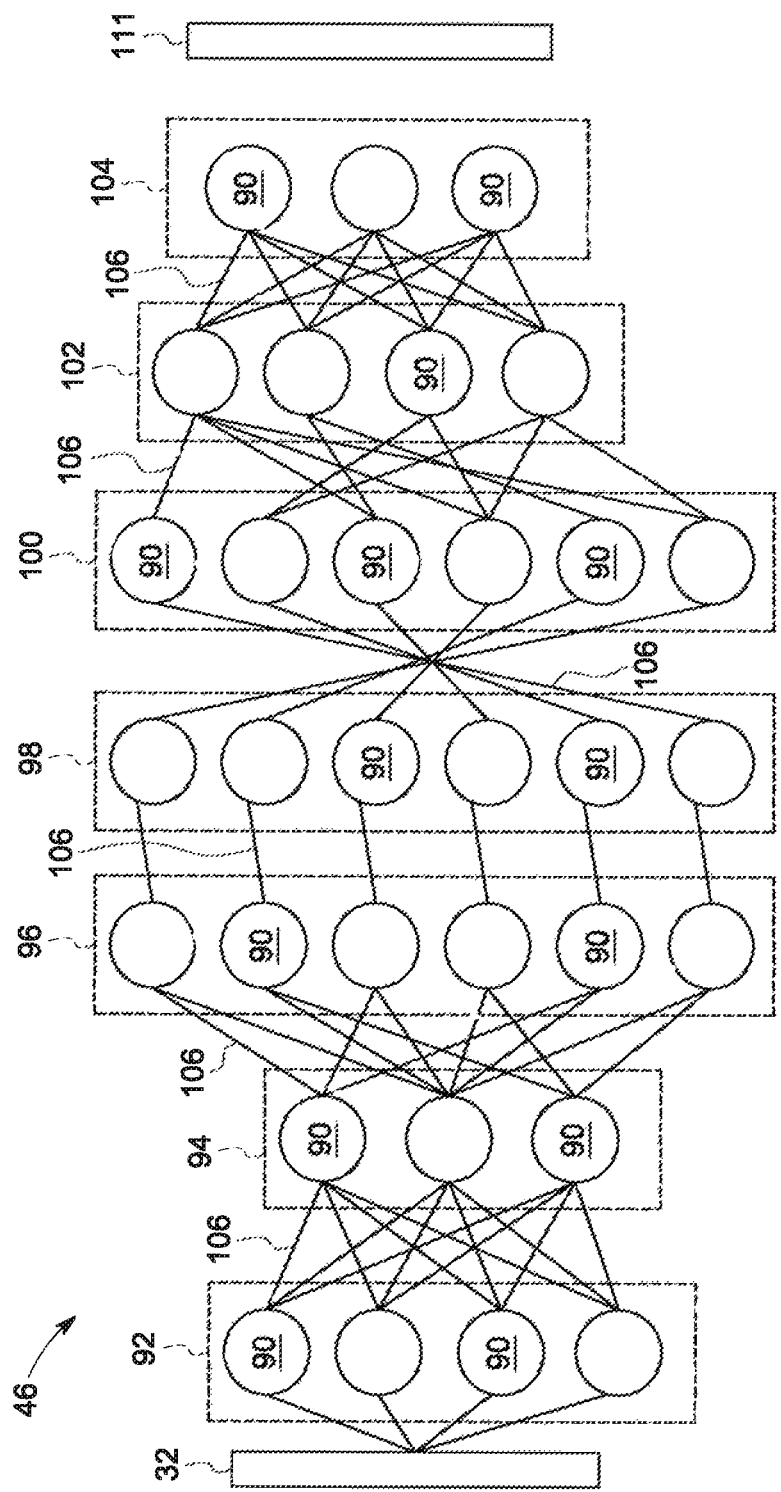
FIG. 10 is a diagram of a machine learning model of the system of FIG. 1, wherein the machine learning model is an artificial neural network, in accordance with an embodiment of the present invention.

Turning now to FIG. 2, a representative study signal 38 with a noise fingerprint 18 is shown. As can be seen, the study signal 38, and the data derived therefrom, may correspond to waveforms in the range of about zero (0) Hz to about two-hundred (200) Hz. In embodiments, the study signal 38 includes the patient's physiological signal, i.e., the cardiac component having the QRS complex with two R-waves 66 and 68. In embodiments, the data, e.g., datum 32 (FIG. 1), corresponding to a study signal 38 may include a representation of the entire signal 38. As briefly discussed above, due to a variety of factors, electromagnetic noise can affect the signal 38 and produce noise fingerprints 18. As can be further seen in FIG. 2, the noise 18 is easily distinguishable from the patient's physiological signal at regions of interest (ROIs) 70 located between the R-waves 66 and 68. Thus, as will be appreciated, in some embodiments, the application 16 (FIG. 1) may adapt the processor 12 to isolate the ROIs 70 from data corresponding to areas of the signal 38 outside of the ROIs 70, and then to process the ROIs 70 with the machine learning model 46 (FIG. 10). In such embodiments, the application 16 may use a peak detector to detect the R-waves 66 and 68 in order to locate and/or isolate the ROIs 70.

In embodiments, the data, e.g., datum 32 (FIG. 1) corresponding to a study signal 38 acquired at a first medical site 58 (FIG. 1), may be transmitted to the server 48 including representations of just the ROIs 70. In embodiments, the ROIs 70 may be isolated by the EP device, e.g., 52, 54 and 56 (FIG. 1), acquiring the signal 38. In other words, in embodiments, the ROIs 70 may be baseline quiescent periods isolated at the medial site, e.g., 58, 60, 62 or at the server site 50 so as to have none of the patient's, e.g., 40, 42, 44, physiological electrical impulses.

Referring now to FIGS. 3-9, various examples of possible noise sources 72, 74, 76, 78, 80, 82 (FIG. 9) effecting a medical site, e.g., 58 (FIGS. 1 and 9), and their corresponding noise fingerprints 20, 22, 24, 26, 28 and 30 (FIGS. 3-8) are shown. Accordingly, a device 72, e.g., a power supply/converter, operating on 60 Hz 120 VAC may generate a noise fingerprint 20 having the characteristics shown in FIG. 3, i.e., superimposed 60 Hz sine waves. A device 74, such as a Mapping System Device, e.g., non-fluoroscopic three-dimensional electrophysiological mapping such as "CARTO", with a bad connection between one of its leads 88 and the patient 40 may generate a noise fingerprint 22 having the characteristics shown in FIG. 4. A muscle artifact (by the patient 40) may generate a noise fingerprint 24 having the characteristics shown in FIG. 5. A cardiac pacer 76 may generate noise fingerprints 26, 28 and 30 having the characteristics shown in FIGS. 6, 7 and/or 8.

Additional sources of noise may include an ablation device, an anesthesia device, a cautery knife, defective patient cables, ground loops, static bleed from linoleum flooring, static charge generated by infusion pumps, irrigated ablation catheters, an imaging device, a monitoring device, lighting equipment, a contrast injector, pacing equipment, preparation tools such as centrifuges, heating devices such as bed warmers, IT equipment, powerlines and/or power supply/transmission equipment (which may include electrical power disturbances, e.g., natural events such as lightening or manmade events such as power discharges, e.g., ARC welding), kitchen/home appliances, and/or other noise sources.

Moving now to FIG. 10, a depiction of the machine learning model 46 as an artificial neural network, in accordance with an embodiment of the present invention, is shown. The neural network 46 may include one or more nodes/neurons 90 which, in embodiments, may be disposed in one or more layers 92, 94, 96, 98, 100, 102, 104. As used herein with respect to a neural network, the term "layer" refers to a collection of simulated neurons that have inputs and/or outputs connected in similar fashion to other collections of simulated neurons. Accordingly, as shown in FIG. 10, the neurons 90 may be connected to each other via one or more connections 106 such that the data, e.g., datum 32 (also shown in FIG. 1) corresponding to the study signals 38 may propagate from an input layer 92, through one or more intermediate/hidden layers 94, 96, 98, 100, 102, to an output layer 104.

Figure 11:
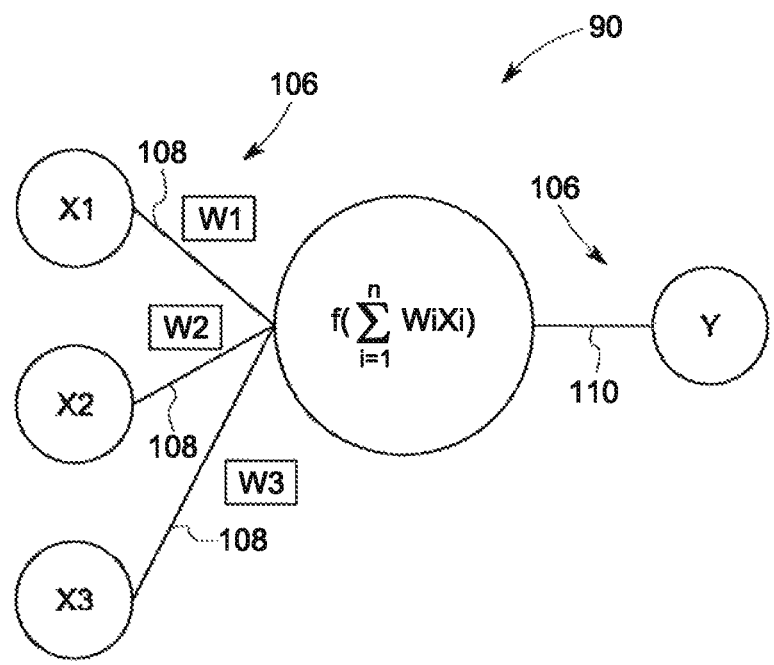
FIG. 11 is a diagram of a neuron of the artificial neural network of FIG. 10, in accordance with an embodiment of the present invention.

As shown in FIG. 11, the connections 106 of an individual neuron 90 may include one or more input connections 108 and one or more output connections 110. Each input connection 108 of a neuron 90 may be an output connection of a preceding neuron, and the output connections 110 of the neuron 90 may be an input connection of one or more subsequent neurons. While FIG. 11 depicts a neuron 90 as having a single output connection 110, it will be understood that neurons 90 may have multiple output connections that transmit/pass the same value. In embodiments, the neurons 90 may be data constructs, e.g., structures, instantiated class objects, matrices, etc., and the input connections 108 may be received by a neuron 90 as weighted numerical values, e.g., floating point or integer values. For example, as shown in FIG. 11, input connections X1, X2, and X3 may be weighted via weights W1, W2, and W3, respectively, summed, and sent/transmitted/passed as output connection Y. As will be appreciated, the processing of an individual neuron 90 may be represented, generally, by the equation:

$$y = f\left(\sum_{i=1}^{n} WiXi\right)$$

where n is the total number of input connections 108 to the neuron 90. In embodiments, the value of Y may be based at least in part on whether the summation of WiXi exceeds a threshold. For example, Y may have a value of zero (0) if the summation of the weighted inputs fails to exceed a desired threshold.

As will be further understood, the input connections 108 of neurons 90 in the input layer 92 (FIG. 10) may be mapped to the data, e.g., datum 32, while the output connections 110 of the neurons 90 in the output layer 104 (FIG. 10) may be mapped to a plurality of known noise fingerprints 111. As used herein: a "known noise fingerprint" refers to a noise fingerprint whose noise source is known; "mapping" an input connection 108 to data acquired from a EP study refers to the manner by which the data, e.g., datum 32, affect/dictate the value of the input connection 108; and "mapping" an output connection 110 to the plurality of known fingerprints 111 refers to the manner by which the value of the output connection 110 selects (or contributes to the selection of) a known noise fingerprint 111 from the plurality based on the value of the output connection 110.

Accordingly, in embodiments, data corresponding to an EP study, e.g., datum 32, is passed/fed to the input layer 92 of the neutral network 46 and propagates through the layers 92, 94, 96, 98, 100, 102 and 104 such that mapped output connections 110 of the output layer 104 select a corresponding known noise fingerprint 111. In other words, data representative of the study signals 38 acquired during an EP study is fed into the neural network 46, which then matches the data to a known noise fingerprint 111, thus, in turn, providing an indication of the type of noise source, e.g., 72, 74, 76, 78, 80, 82, etc., (FIG. 9) likely responsible for generating the noise in the study signal 38.

Figure 9:
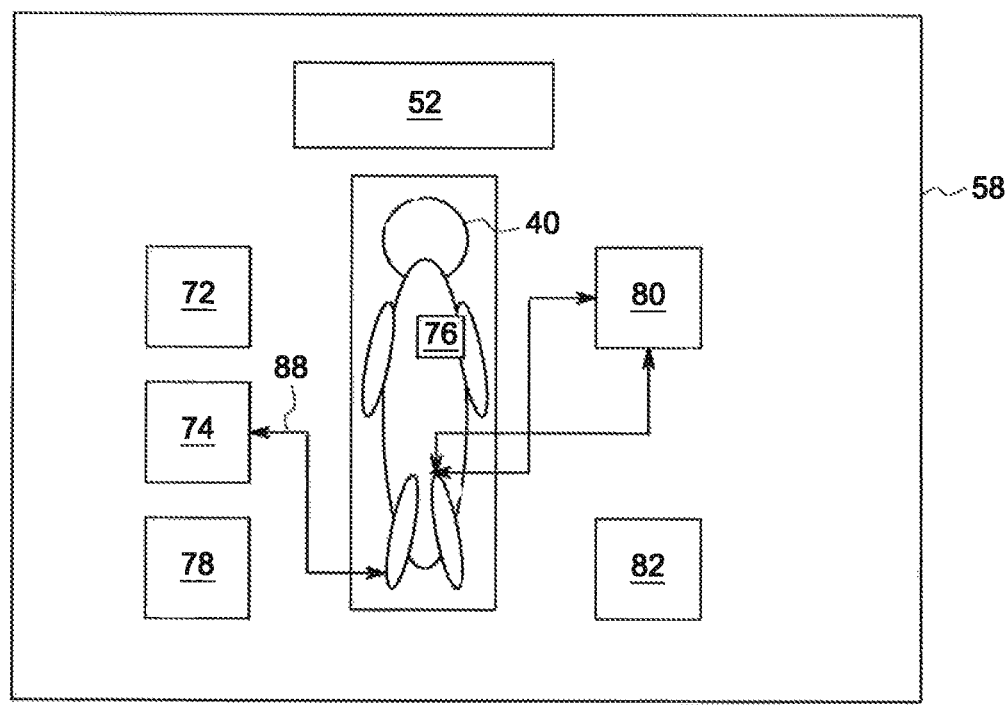
FIG. 9 is a block diagram of possible noise sources in the one or more EP studies of the system of FIG. 1, in accordance with an embodiment of the present invention.

Accordingly, in embodiments, the application 16 (FIG. 1) may transmit, to a medical site, a noise source indicator 112 (FIG. 1), corresponding to a noise source, e.g., 72, 74, 76, 78, 80, 82, etc., of a known noise fingerprint (FIG. 1) that was selected/matched to data provided to the application 16 by the medical site. For example, medical site 58 (FIG. 1) may acquire an EP signal 38 from a patient 40 wherein the EP signal has noise. The EP signal 38 is used to generate the data 32 which is transmitted to the server site 50 for analysis by the Application 16. The application 16 passes the data 32 to the neural network 46 which identifies a noise fingerprint (similar to the one shown in FIG. 3) within the data 32 corresponding to a generator 72 (FIG. 9). The application 16 then transmits a noise source indicator 112 back to the medical site 58 indicating that the source of the noise during the corresponding EP study was/is likely the generator 72.

In embodiments, the training set for the neural network 46 may include the known noise fingerprints 111. Thus, embodiments of the neural network 46 may be able to identify as many types of noise fingerprints as the training set provides for. As will be understood, however, in embodiments, the neural network 46 may recognize that a noise fingerprint is present within EP data, provided from a medical site, but be unable to match it to a known noise fingerprint 111. In other words, the neural network 46 may detect the presence of a noise fingerprint which is outside of its training set. In such a case, the application 16 (FIG. 1) may store the recognized noise fingerprint in the memory device 14 for subsequent analysis by a human, and/or until the training set for the neural network 46 is updated to specify a known noise source for the previously unmatchable noise fingerprint. Thus, embodiments of the present invention may provide for a digital library of saved noise fingerprints that are unknown to the neural network 46 until a human, or other analyzer, has discovered a corresponding noise source.

In certain aspect of the present invention, the application 16 may provide for an interface, e.g., a web-based user interface or other type of network interface, that allows operators of the EP devices 52, 54 and 56 (FIG. 1) to provide known noise sources for previously unknown noise fingerprints. In other words, the application 16 may allow the medical sites 58, 60, 62 (FIG. 1) to assist in training the neural network 46 by enabling the medical sites 58, 60 and 62 to update the training set of known noise fingerprints 111 based on discoveries made at the medical sites 58, 60 and 62.

While the machine learning model 46 is depicted in FIGS. 10 and 11 as an artificial neural network, it will be understood the machine learning model 46 may take other forms. In embodiments, the learning model 46 may implement linear regression, logistic regression, supervised learning, unsupervised learning, or other suitable machine learning approaches.

Figure 12:
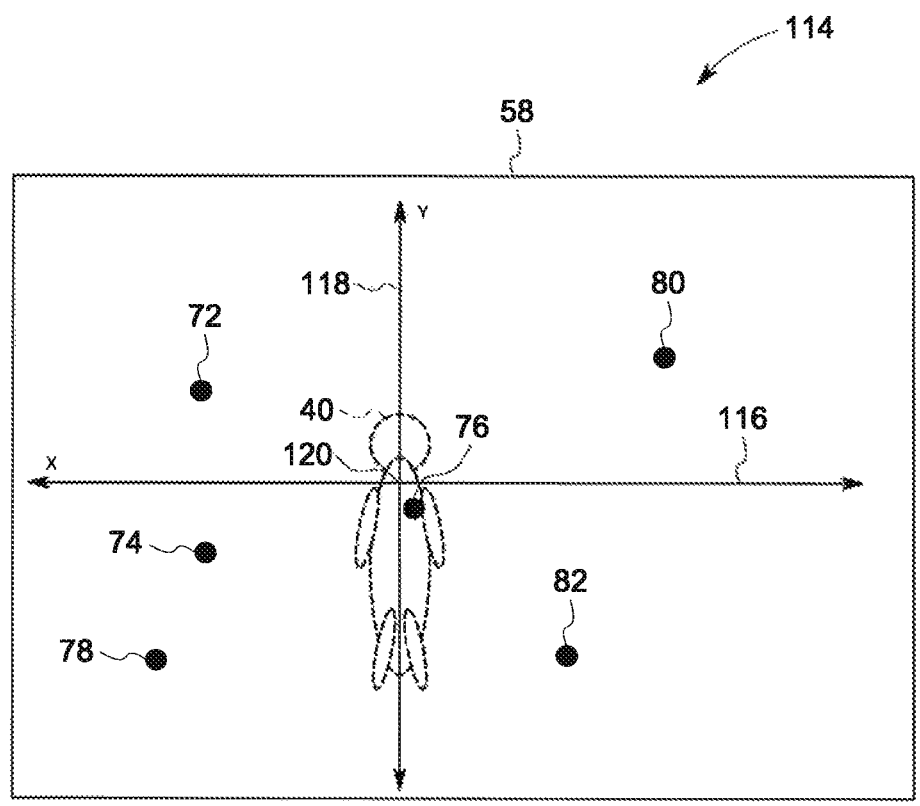
FIG. 12 is a diagram of a noise map generated by the system of FIG. 1, in accordance with an embodiment of the present invention.

Referring now to FIGS. 9 and 12, in embodiments, the application 16 (FIG. 1) may further adapt the at least one processor 12 (FIG. 1) to generate a noise map 114 (FIG. 12) that depicts the location of noise sources, e.g., 72, 74, 76, 78, 80, 82 (FIGS. 9 and 12) at a site, e.g., 58 (also shown in FIG. 1), with respect to a coordinate system, e.g., x-axis 116 and y-axis 118. While FIG. 12 depicts the coordinate system 116 and 118 as being a 2D Cartesian system having an origin 120 centered at and/or near the center of the site 58, e.g., room in which EP studies are performed, it will be understood that other types of coordinate systems, e.g., 3D Cartesian, polar, spherical, and/or origins may be used as well. In embodiments the machine learning model 46 may be able to distinguish between the same, and/or similar, noise sources disposed at different orientations and/or positions from the origin 120. For example, the machine learning model 46 may be able to distinguish the noise fingerprints of a power converter disposed at five (5) feet, ten (10) feet, etc.

In embodiments, the application 16 (FIG. 1) may further adapt the at least one processor 12 to transmit to a medical site, e.g., 58, a noise map 114 (FIG. 1) generated based at least in part on receiving data, e.g., datum 32, from the medical site 58. The application 16 may also adapt the at least one processor 12 to generate custom filters, for mitigating the effect of the identified noise source in the EP signals 38, based on the noise fingerprints identified in data corresponding to a particular medical site, e.g., 58. The custom filters may then be transmitted back to the medical site for use during EP study procedures.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, the system 10 may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, the software application 16 that adapts the controller, i.e., at least one processor 12, to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory ("DRAM"), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for analyzing noise in one or more electrophysiology studies is provided. The system includes at least one processor and at least one memory device. The memory device stores an application that adapts the at least one processor to: identify, based at least in part on a machine learning model, one or more noise fingerprints within data derived at least in part from one or more study signals acquired from one or more patients during the one or more electrophysiology studies. In certain embodiments, the machine learning model is an artificial neural network. In certain embodiments, at least one of the one or more noise fingerprints corresponds to at least one of an ablation device, an anesthesia device, a cautery knife, an imaging device, a monitoring device, lighting equipment, a contrast injector, pacing equipment, IT equipment, and powerlines. In certain embodiments, at least two of the one or more electrophysiology studies are performed at different medical sites. In certain embodiments, the data provided to the machine learning model corresponds to waveforms. In certain embodiments, the waveforms have a range about 0 Hz to about 200 Hz. In certain embodiments, the application further adapts the controller to isolate a region of interest within the data. The region of interest corresponds to a portion between R-waves of a study signal of the one or more study signals. In certain embodiments, the application further adapts the controller to generate a noise map of one or more noise sources based at least in part on the one or more noise fingerprints.

Other embodiments provide for a method for analyzing noise in one or more electrophysiology studies. The method includes identifying, based at least in part on a machine learning model executing on at least one processor, one or more noise fingerprints within data derived at least in part from one or more study signals acquired from one or more patients during the one or more electrophysiology studies. In certain embodiments, the machine learning model is an artificial neural network. In certain embodiments, the method further includes receiving, at the at least one processor, portions of the data from different medical sites.

In certain embodiments, the method further includes isolating a region of interest within the data. The region of interest corresponds to a portion between R-waves of a study signal of the one or more study signals. In certain embodiments, at least one of the one or more noise fingerprints corresponds to at least one of an ablation device, an anesthesia device, a cautery knife, an imaging device, a monitoring device, lighting equipment, a contrast injector, pacing equipment, IT equipment, and powerlines. In certain embodiments, the method further includes transmitting, by way of the at least one processor, a noise source indicator to a medical site. The noise source indicator corresponds to an identified noise fingerprint and a noise source. In certain embodiments, the method further includes generating a noise map of one or more noise sources based at least in part on the one or more noise fingerprints. In certain embodiments, the method further includes transmitting, by way of the at least one processor, the noise map to a medical site.

Yet still other embodiments provide for a non-transitory computer readable medium including instructions. The instructions adapt at least one processor to: identify, based at least in part on a machine learning model, one or more noise fingerprints within data derived at least in part from one or more study signals acquired from one or more patients during one or more electrophysiology studies. In certain embodiments, the machine learning model is an artificial neural network. In certain embodiments, the instructions further adapt the at least one processor to transmit a noise source indicator to a medical site. The noise source indicator corresponds to an identified noise fingerprint and a noise source. In certain embodiments, the instructions further adapt the at least one processor to isolate a region of interest within the data. The region of interest corresponds to a portion between R-waves of a study signal of the one or more study signals.

Accordingly, by using machine learning to identify noise fingerprints within data corresponding to EP signals, some embodiments of the present invention provide for automated identification of noise sources within the EP study medical context. As will be appreciated, the automated identification of noise fingerprints, by some embodiments of the present invention, may provide for faster and more accurate analysis of noise within EP studies.

Further, by using a neural network to identify noise fingerprints within EP study data, some embodiments of the present invention provide for the detection of noise fingerprints that a human analyzer is likely to overlook. Thus, some embodiments of the present invention provide for improved detection of noise within an EP study over traditional approaches that rely on human quantitative analysis. Thus, some embodiments of the present invention provide for extremely high sensitivity to the smallest potential coupled interfering-noise signal.

Further still, by utilizing a processor to identify noise fingerprints within EP study data, some embodiments of the present invention provide for rapid noise fingerprinting of common disturbing sources, e.g., line frequency, muscle tremors, magnetic fields, etc. Thus, some embodiments provide for greater control over EP study procedures and/or quality of trace recording.

Yet further still, some embodiments of the present invention may provide for the support of retrospective study analysis to determine the sources of noise present in an EP study at any point in the recorded data, i.e., where data is available.

Yet further still, by generating a noise map, some embodiments of the present invention provide for a visual presentation of noise sources within a medical site.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined in part by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for analyzing noise in one or more electrophysiology studies, the system comprising:
at least one processor; and,
at least one memory device that stores an application that adapts the at least one processor to:
acquire one or more entire electrophysiology study signals in real time from one or more electrophysiology patients via one or more sensors operative to sense electrical activity produced by a patient, the one or more entire electrophysiology study signal being a waveform in a range of about 0 Hz to about 200 Hz and including a cardiac component and an electromagnetic noise component;
isolate a region of interest within an entire electrophysiology study signal, the region of interest corresponding to a portion between R-waves of the entire electrophysiology study signal, the region of interest representing the electromagnetic noise component substantially without the cardiac component;
pass the region of interest to an input layer of a machine learning model trained from a set of known noise fingerprints representative of sources of electromagnetic noise;
identify a source of electromagnetic noise in the entire electrophysiology study signal based on the trained machine learning model; and
transmit a noise source indicator corresponding to the source of electromagnetic noise.

2. The system of claim 1, wherein the machine learning model is an artificial neural network trained on noise fingerprints.

3. The system of claim 1, wherein at least one of the set of known noise fingerprints corresponds to at least one of an ablation device, an anesthesia device, a cautery knife, an imaging device, a monitoring device, lighting equipment, a contrast injector, pacing equipment, IT equipment, and powerlines.

4. The system of claim 1, wherein at least two of the one or more electrophysiology studies are performed at different medical sites.

5. The system of claim 1, wherein the application further adapts the processor to: generate a noise map of one or more noise sources based at least in part on the set of known noise fingerprints.

6. A method for analyzing noise in one or more electrophysiology studies, the method comprising:

acquiring one or more entire electrophysiology study signals in real time from one or more electrophysiology patients via one or more sensors operative to sense electrical activity produced by a patient, the one or more entire electrophysiology study signal being a waveform in a range of about 0 Hz to about 200 Hz and including a cardiac component and an electromagnetic noise component;

isolating a region of interest within an entire electrophysiology study signal, the region of interest corresponding to a portion between R-waves of the entire electrophysiology study signal, the region of interest representing the electromagnetic noise component substantially without the cardiac component;

passing the region of interest to an input layer of a machine learning model trained from a set of known noise fingerprints representative of sources of electromagnetic noise; and identifying a source of electromagnetic noise in the entire electrophysiology study signal, based on the trained machine learning model.

7. The method of claim 6, wherein the machine learning model is an artificial neural network.

8. The method of claim 6, wherein, at least one of the set of known noise fingerprints corresponds to at least one of an ablation device, an anesthesia device, a cautery knife, an imaging device, a monitoring device, lighting equipment, a contrast injector, pacing equipment, IT equipment, and powerlines.

9. The method of claim 6 further comprising:

transmitting, by way of at least one processor, a noise source indicator to a medical site, the noise source indicator corresponding to an identified noise fingerprint and a noise source.

10. The method of claim 6 further comprising:

generating a noise map of one or more noise sources based at least in part on the set of known noise fingerprints.

11. The method of claim 10 further comprising:

transmitting, by way of at least one processor, the noise map to a medical site.

12. A non-transitory computer readable medium comprising instructions that adapt at least one processor to:

acquire one or more entire electrophysiology study signals in real time from one or more electrophysiology patients via one or more sensors operative to sense electrical activity produced by a patient, the one or more entire electrophysiology study signal being a waveform in a range of about 0 Hz to about 200 Hz and including a cardiac component and an electromagnetic noise component;

isolate a region of interest within an entire electrophysiology study signal, the region of interest corresponding to a portion between R-waves of the entire electrophysiology study signal, the region of interest representing the electromagnetic noise component substantially without the cardiac component;

pass the region of interest to an input layer of a machine learning model trained from a set of known noise fingerprints representative of sources of electromagnetic noise;

identify a source of electromagnetic noise in the entire electrophysiology study signal, based on the trained machine learning model.

13. The non-transitory computer readable medium of claim 12, wherein the machine learning model is an artificial neural network.

14. The non-transitory computer readable medium of claim 12, wherein the instructions further adapt the at least one processor to:

transmit a noise source indicator to a medical site, the noise source indicator corresponding to an identified noise fingerprint and a noise source.

* * * * *